(12) United States Patent
Ebihara et al.

(10) Patent No.: US 9,420,817 B2
(45) Date of Patent: Aug. 23, 2016

(54) AGENT FOR AMELIORATION OF DYSPHAGIA, AND PHARMACEUTICAL OR FOOD COMPOSITION COMPRISING THE SAME

(75) Inventors: Takae Ebihara, Sendai (JP); Satoru Ebihara, Sendai (JP); Yoko Shimagami, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 756 days.

(21) Appl. No.: 12/257,830

(22) Filed: Oct. 24, 2008

(65) Prior Publication Data

US 2009/0281182 A1 Nov. 12, 2009

Related U.S. Application Data

(63) Continuation of application No. PCT/JP2007/056823, filed on Mar. 29, 2007.

(30) Foreign Application Priority Data

Apr. 24, 2006 (JP) .................................. 2006-119319

(51) Int. Cl.
*A61K 31/23* (2006.01)
*A61K 31/231* (2006.01)
*A23L 1/30* (2006.01)

(52) U.S. Cl.
CPC . *A23L 1/30* (2013.01); *A61K 31/23* (2013.01); *A61K 31/231* (2013.01)

(58) Field of Classification Search
CPC .............................. A61K 31/23; A61K 31/231
See application file for complete search history.

(56) References Cited

U.S. PATENT DOCUMENTS

| | | | | |
|---|---|---|---|---|
| 6,159,473 | A * | 12/2000 | Watkins et al. | 424/734 |
| 6,333,421 | B1 * | 12/2001 | Yazawa et al. | 554/229 |
| 7,414,075 | B2 * | 8/2008 | Tani et al. | 514/546 |
| 2003/0082249 | A1 | 5/2003 | Gordon | |
| 2005/0239883 | A1 * | 10/2005 | Tani et al. | 514/546 |
| 2006/0287390 | A1 * | 12/2006 | Sagawa et al. | 514/546 |

FOREIGN PATENT DOCUMENTS

| | | |
|---|---|---|
| EP | 1 069 105 A1 | 1/2001 |
| JP | 11-246478 A | 9/1999 |
| JP | 2005-161 | 1/2005 |
| WO | WO 96/40079 | 12/1996 |
| WO | WO 2004/058301 A1 | 7/2004 |

OTHER PUBLICATIONS

U.S. Appl. No. 11/695,198, filed Apr. 2007, Ito et al.*
Kobata et al. 1999, Nordihydrocapsiate, a new capsinoid from the fruits of a nonpungent pepper, *Capsicum annum*. J. Nat. Prod. vol. 62, pp. 335-336.*
Iida et al. 2003, "TRPV1 activation and induction of nociceptive response by a non-pungent capsaicin-like compound, capsiate." Neuropharmacology, vol. 44, pp. 958-967.*
Ebihara, T., et al. "Capsaicin Troche for Swallowing Dysfunction in Older People," JAGS, vol. 53, No. 5, May 2005, pp. 824-828.
Sachiko Hachiya, et al., "Effects of CH-19 Sweet, a Non-Pungent Cultivar of Red Pepper, on Sympathetic Nervous Activity, Body Temperature, Heart Rate, and Blood Pressure in Humans", Biosci. Biotechnol. Biochem, 71 (3), 671-676, 2007.
Japanese Office Action issued Jul. 31, 2012 in Patent Application No. 2008-513113 with Partial English Translation.
Hidetada Sasaki et al., "Prevention of Inapparent Aspiration (the Effect of Capsicum)", Chemical Treatment Field, vol. 14, No. 2, 1998, pp. 91-97 (with Partial English Translation).
Perceived Irritation during Ingestion of Capsaicin or Piperine: Comparison of Trigeminal and Non-trigeminal Areas, Heike Rentmeister-Bryant and Barry G. Green, Oxford University Press, Downloaded from http://chemse.oxfordjournals.org/ by guest on Dec. 5, 2011, Chem. Senses vol. 22, pp. 257-266, 1997.
Pierangelo Geppetti, et al., British Journal of Pharmacology (2004) 141, 1313-1320, 2004 Nature Publishing Group; "Activation and Sensitisation of the Vanilloid Receptor: Role in Gastrointestinal Inflammation and Function".
Hidetaka Sakai, et al., "Antibiotics & Chemotherapy", vol. 14, No. 2, 1998, pp. 305-311, with attached partial English translation.

* cited by examiner

*Primary Examiner* — Kara R McMillian
(74) *Attorney, Agent, or Firm* — Oblon, McClelland, Maier & Neustadt, L.L.P.

(57) ABSTRACT

Disclosed is an agent for ameliorating dysphagia containing capsinoid as an active ingredient. Also disclosed is a pharmaceutical composition or food composition containing the agent. The agent, pharmaceutical composition or food can be administered to a subject suffering from dysphagia such as elderly person.

32 Claims, 1 Drawing Sheet

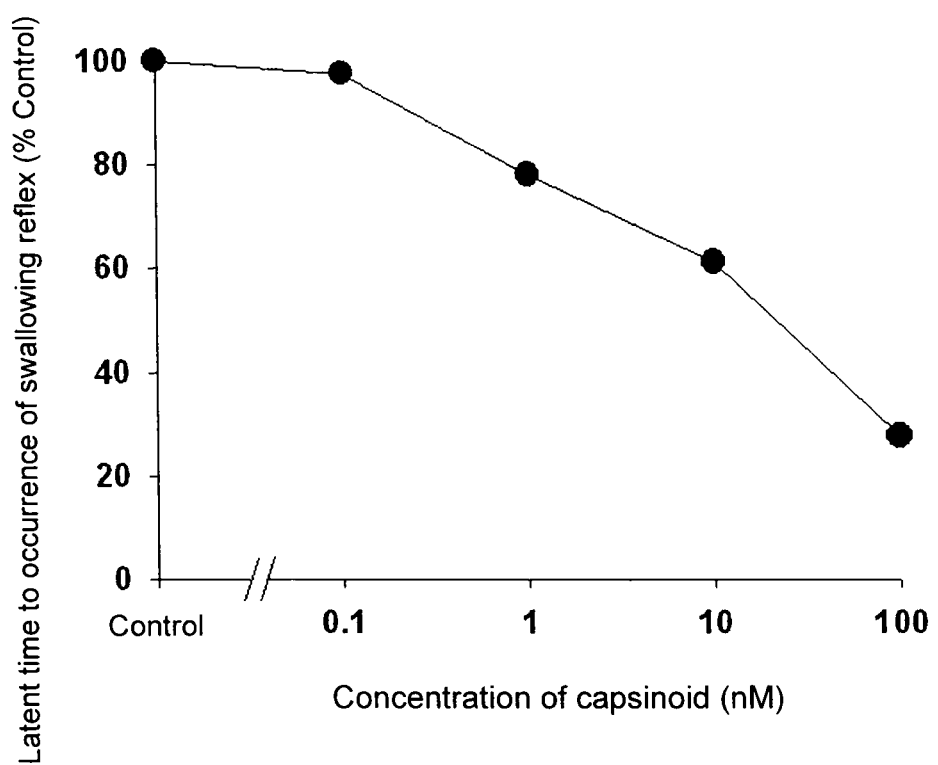

AGENT FOR AMELIORATION OF DYSPHAGIA, AND PHARMACEUTICAL OR FOOD COMPOSITION COMPRISING THE SAME

TECHNICAL FIELD

The present invention relates to an agent for ameliorating dysphagia, and a pharmaceutical composition or a food composition containing the same.

BACKGROUND ART

As the population ages, elderly people suffering from dysphagia are increasing. Many elderly people may have difficulty in swallowing foods and develop symptoms of dysphagia. In many cases, dysphagia may cause aspiration (entry of a substance in the oral cavity into the airway), and entry of the aspirated substance into the lung may cause bacterial infection, resulting in pneumonia. Therefore, amelioration of dysphagia to prevent the aspiration is expected to be effective for reducing senile pneumonia.

On the other hand, many patients suffering from aftereffects of cerebral stroke frequently develop pneumonia. In recent years, it has became clear that, among patients suffering from cerebral stroke, patients having cerebrovascular disorders in the basal ganglion have a higher incidence of pneumonia. A dopamine receptor produced from the nigrostriatum is originally present in the basal ganglion, so a damage in the basal ganglion may affect various functions to be controlled by a brain dopamine. The dopamine adjusts the amount of substance P secreted from a sensory branch in the vagus nerve to the pharynx or airway. The substance P plays an important role in perception in the pharynx or airway, and a decrease in the amount of secreted substance P may disturb swallowing reflex in the pharynx and may disturb cough reflex in the airway.

Patent Document 1 discloses an agent for ameliorating dysphagia, which contains a polyphenol as an active ingredient. On the other hand, Non-Patent Document 1 discloses a capsaicin troche for dysphagia in elderly people. However, there is a problem that, if capsaicin is used in an amount sufficient to ameliorate dysphagia, pungent taste may be caused.

The capsinoid, which is known as a *capsicum* component as well as capsaicin, is known to have an activation action on energy metabolism (Patent Document 2: JP 11-246478 A), weight loss effect (Patent Document 3: JP 2001-026538 A), accelerating action on oxygen consumption (Non-Patent Document 2: Biosci. Biotech. Biochem: 65(12) 2735-40 (2001)), etc. Meanwhile, an experiment in which a person ingests "CH-19 sweet" containing a capsinoid has been confirmed that the capsinoid has a hyperthermic action and accelerating action on oxygen consumption in the human (Non-Patent Document 3: Biosci. Biotech. Biochem: 65(9) 2033-2036 (2001)). However, it has not been known that the capsinoid has an ameliorating action on dysphagia.

Patent Document 1: JP 2004-107285 A
Patent Document 2: JP 11-246478 A
Patent Document 3: JP 2001-026538 A
Non Patent Document 1: JAGS, 53, p. 824-828. 2005
Non Patent Document 2: Biosci. Biotech. Biochem: 65(12) 2735-40 (2001)
Non Patent Document 3: Biosci. Biotech. Biochem: 65(9) 2033-2036 (2001)

DISCLOSURE OF THE INVENTION

Problems to be Solved by the Invention

An object of the present invention is to provide an agent for ameliorating dysphagia, which is effective for ameliorating dysphagia, is easily ingested by elderly people, and is useful as a pharmaceutical and a food.

Means for Solving the Problems

The inventors of the present invention have made extensive studies to solve the above-mentioned problems, with the result that the inventors have found out that administration of a small amount of capsinoid is effective for ameliorating dysphagia, and thus accomplished the present invention.

That is, the present invention is as follows:

(1) an agent for ameliorating dysphagia containing a capsinoid;

(2) a pharmaceutical composition containing the agent for ameliorating dysphagia;

(3) a food composition containing the agent for ameliorating dysphagia;

(4) the food composition, in which a capsinoid content is 1 nmol/kg to 10 mmol/kg;

(5) the food composition, in which the food composition is a troche;

(6) a method of ameliorating dysphagia including administering a composition containing a capsinoid to a subject suffering from dysphagia; and (7) a use of a capsinoid in production of a pharmaceutical composition for ameliorating dysphagia.

BRIEF DESCRIPTION OF THE DRAWING

FIG. 1 shows a relationship between a concentration of capsinoid and a latent time between administration of a capsinoid and the initiation of swallowing reflex. The ordinate axis represents a mean latent time of three subjects where the value of the control is defined as 100%, while the abscissa axis represents a concentration of the capsinoid.

BEST MODE FOR CARRYING OUT THE INVENTION

Hereinafter, the present invention is described in detail.

The capsinoid in the present invention refers to a fatty acid ester of a vanillyl alcohol. Examples of representative component thereof include, but are not limited to, capsiate, dihydrocapsiate, and nordihydrocapsiate, which have been confirmed as components contained in capsicums, and further include a fatty acid ester of various linear or branched fatty acids and vanillyl alcohols, whose fatty acid chain length is close to the length of capsiate or nordihydrocapsiate such as vanillyl decanoate, vanillyl nonanoate, or vanillyl octanoate. Capsiate (4-hydroxy-3-methoxybenzyl(E)-8-methyl-6-nonenoate, hereinafter, sometimes abbreviated as "CST"), dihydrocapsiate (4-hydroxy-3-methoxybenzyl 8-methyl-nonanoate, hereinafter, sometimes abbreviated as "DCT"), and nordihydrocapsiate (4-hydroxy-3-methoxybenzyl 7-methyl-octanoate, hereinafter, sometimes abbreviated as "NDCT") have the following respective chemical formulae.

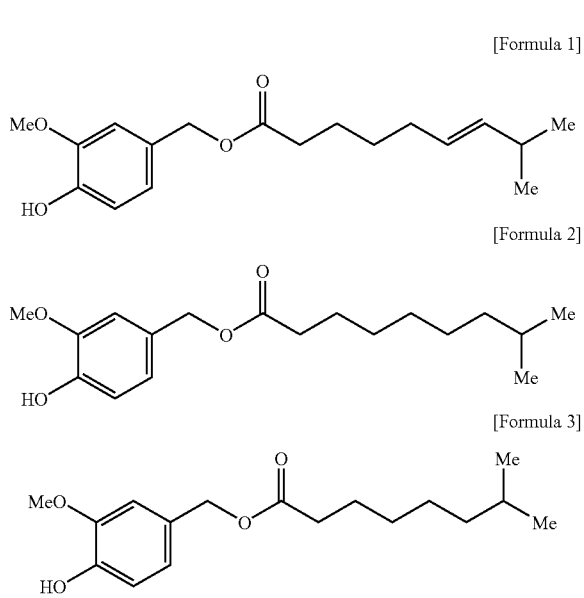

[Formula 1]

[Formula 2]

[Formula 3]

A plant body belonging to the genus *Capsicum* contains a large amount of capsinoid, and hence the capsinoid can be prepared from a plant body belonging to the genus *Capsicum* (hereinafter, referred to as "*capsicum*") and/or a fruit of the plant by purification/isolation. A *capsicum* that is used in purification may be derived from a conventional *capsicum* variety having pungency such as "Nikko" or "Goshiki", but any species of *capsicum* may be used as long as the *capsicum* contains capsinoid. Particularly, a conventional non-pungent variety of *capsicum* such as "CH-19 sweet", "Manganji", "Fushimiamanaga", shishitou, or green pepper contains a large amount of capsinoid, so the capsicums above may be suitably used. Moreover, a non-pungent variety of "CH-19 sweet" is particularly preferably used because its capsinoid content is high. Herein, the term "CH-19 sweet" includes "CH-19 sweet" and progeny related varieties derived from "CH-19 sweet", etc., and herein, the term "CH-19 sweet" is used in the sense that the term includes all of them.

It has been reported that a non-pungent fixed variety of *capsicum*, "CH-19 sweet", which had been selected and fixed by Yazawa et al. as a *capsicum* having less pungency, contains few capsaicinoid compounds having a pungency and nociceptive activity as general capsicums (capsaicin, dihydrocapsaicin, etc.) (hereinafter, often simply referred to as "capsaicinoid"). Thus, "CH-19 sweet" is particularly preferable as a material for an agent for ameliorating dysphagia for oral ingestion. In addition, "CH-19 sweet" contains large amounts of CST, DCT, and NDCT (JP 11-246478 A), and is preferable. Further, the capsinoid has been confirmed to exist also in other plants belonging to the genus *Capsicum* (Journal of the Japanese Society for Horticultural Science 58, 601-607).

The purification/isolation of capsinoid from the plant belonging to the genus *Capsicum* may be performed by using technologies such as solvent extraction, chromatography including silica gel chromatography, and high-performance liquid chromatography for preparation, which are well known to a person skilled in the art, singly or in an appropriate combination. That is, the capsinoid may be isolated and purified as follows: ethanol extraction of a *capsicum* plant body is performed under acid condition, and the extracted product is adsorbed to an adsorbent and eluted with ethanol containing an acidic substance, followed by vacuum concentration, thereby isolating and purifying the capsinoid (JP 2004-18428 A). Specifically, for example, a fraction containing capsinoid can be obtained by: drying a *capsicum* fruit of "CH-19 sweet" or the like; performing extraction with various organic solvents such as ethyl acetate and hexane; and performing molecular distillation for the resultant extracted oil.

In addition, capsinoid may be synthesized by, for example, a transesterification reaction using a corresponding fatty acid ester and vanillyl alcohol as starting materials as described in JP 11-246478 A. Alternatively, the capsinoid may be synthesized based on its structural formula by other reaction technique that is known to a person skilled in the art. Moreover, capsinoid may be easily prepared by a synthesis method using an enzyme. That is, for example, in accordance with a method described in JP 2000-312598 A or a method of Kobata et al. (Biosci. Biotechnol. Biochem., 66(2), 319-327, 2002), a desired capsinoid compound may be obtained by using a reverse reaction of lipase using a fatty acid ester corresponding to the desired compound and/or a compound having such fatty acid such as triglyceride and vanillyl alcohol as substrates. Meanwhile, the quantitative analysis of the capsinoid may appropriately be performed by high-performance liquid chromatography (HPLC). Conditions of HPLC may easily be set by a person skilled in the art, but the analysis may be performed by a method described in, for example, JP 2004-18428 A.

The agent for ameliorating dysphagia of the present invention contains capsinoid as an active ingredient. When the capsinoid is brought into contact with the oral cavity, pharynx, or airway as shown in Examples, it is possible to induce or ameliorate cough reflex and swallowing reflex without causing pungency. The agent for ameliorating dysphagia of the present invention may contain a very small amount of capsaicinoid in addition to the capsinoid as long as the effect of the present invention is not impaired. However, the ratio of capsinoid and capsaicinoid in the agent for ameliorating dysphagia is preferably 4,000:1 to 1:0, more preferably 2,000:1 to 1:0. Particularly preferably, the agent contains substantially no capsaicinoid.

In the present invention, the capsinoid may be a single compound or a mixture of two or more arbitrary compounds. In addition, the capsinoid to be used may contain a free fatty acid, vanillyl alcohol, and the like, which are products obtained by degradation of the capsinoid. Moreover, the capsinoid may be a purified product or a synthesized product, or may be a composition containing capsinoid, such as a *capsicum*-dried product, *capsicum* oil, or the above-mentioned extracted product containing capsinoid.

The agent for ameliorating dysphagia of the present invention may be ingested in the form of a pharmaceutical composition or a food composition. The pharmaceutical composition or food composition may be produced by the same method as that for a general pharmaceutical or food by using a material to be used for a general oral or nasal pharmaceutical or food as long as the food or pharmaceutical composition contains the capsinoid, which is an active ingredient of the agent for ameliorating dysphagia of the present invention.

The form of the pharmaceutical composition or food composition of the present invention is not particularly limited as long as the composition can be ingested orally or nasally. However, the capsinoid contained as an active ingredient is preferably brought into direct contact with the pharynx. Specific examples of the form include a troche, tablet, gum, spray, and propellant. The troche is more preferably in the form of a troche with a hole because the form can decrease the risk of obstruction of the airway when aspiration occurred. Meanwhile, depending on its dosage form, the pharmaceutical composition or food composition of the present invention may contain a pharmaceutically acceptable vehicle such as lactose, corn starch, sucrose, glucose, sorbitol, or crystalline cellulose. In the case where the composition is in a liquid form, distilled water for injection, physiological saline, an aqueous ethanol solution, or the like may be used as a solvent, and the composition may contain a dispersant. In addition, the composition may further contain a surfactant, flavoring substance, pH adjuster, buffer, stabilizer, preservative, or the like. As the surfactant, any of a non-ionic surfactant, cation surfactant, or an ion surfactant may be used, but the non-ionic surfactant is preferable. In particular, polyoxyethylene sorbitan monolaurate, polyoxyethylene sorbitan monostearate, or polyoxyethylene sorbitan monopalmitate is preferable.

The capsinoid content in the pharmaceutical composition or food composition of the present invention is preferably 1 nmol/kg to 10 mmol/kg, more preferably 10 nmol/kg to 1 mmol/kg, particularly preferably 10 nmol/kg to 100 nmol/kg. In addition, the amount of the capsinoid to be administered or ingested is preferably 0.001 nmol to 1 mmol/dose, more preferably 0.01 nmol to 0.01 mmol/dose, particularly preferably 0.01 nmol to 10 nmol/dose. The number of doses of the pharmaceutical composition or food composition of the present invention is not particularly limited, but the number is preferably one to three doses/day, particularly preferably three doses/day. The time of the administration or ingestion is not particularly limited, but the pharmaceutical composition or food composition of the present invention is preferably administered or ingested before meal or the like.

EXAMPLES

Hereinafter, the present invention is described in more detail by way of Examples.

Production Example

A fruit of "CH-19 sweet" was pulverized and freeze-dried, and the oil content in the fruit was extracted with three times the volume of hexane in a Soxhlet extractor. Thereafter, the solvent was evaporated to dryness, to thereby prepare an extracted composition. To the extracted composition was added 25% by weight of tricaprylin (manufactured by RIKEN VITAMIN CO., LTD., M-2), and molecular distillation was performed using a down-flow thin film molecular distillation apparatus manufactured by Taika Kogyo Co., Ltd. (distillation and heating area 0.024 m$^2$, capacitor area 0.0088 m$^2$) under conditions of distillation and heating temperature: 180° C., vacuum: 12 to 14 Pa, and fat and oil feeding amount: 1.1 g/min, to thereby obtain an extracted oil with the capsinoid content of about 9.5%. The components and the ratio of the capsinoids in the extracted oil were found to be nordihydrocapsiate:capsiate:dihydrocapsiate=17:60:23. In addition, the extracted oil was estimated to contain about 0.005% of capsaicinoid.

In the following Examples, 1 mL of an emulsifier (Tween 80) and 1 mL of 99.7% ethanol were added to 70 µL of the resultant extracted oil immediately before use, and the mixture was diluted with physiological saline (Otsuka) in Example 1 or with distilled water in Example 2, to thereby prepare solutions containing different concentrations of capsinoid. In the same way as above, 1 mL of an emulsifier (Tween 80) and 1 mL of 99.7% ethanol were added to 30.5 mg of capsaicin (manufactured by Sigma-Aldrich) immediately before use, and the mixture was diluted with physiological saline (Otsuka) in Example 1 or with distilled water in Example 2, to thereby prepare solutions containing different concentrations of capsaicin.

Example 1

Cough Receptor Sensitivity Test

Seventeen healthy adults (mean age 36±2.6) inhaled the capsaicin solution prepared in Production Example (0.49 to 1,000 µM) by a nebulizer for 15 seconds at intervals of one minute, and the concentrations for causing five or more coughs by one aspiration (C5) were determined.

At a later date, the same test was performed for the same test subjects using the capsinoid solutions (0.49 to 1,000 µM) to determine C5, followed by comparison between C5 of the capsaicin solution and C5 of the capsinoid solution.

As a result, it was found that the C5 of the capsaicin solution and the C5 of the capsinoid solution were 2.02 µM and 86.4 µM, respectively, and there was a 43-fold difference between the concentrations. On the other hand, the pungency degrees of the capsinoid, determined by the Scoville method, were found to be 1/1,000 compared with the capsaicin. Thus, it was shown that the capsinoid could induce cough reflex without causing pungency.

Example 2

Amelioration of Dysphagia

A catheter was inserted into three elderly men and women suffering from underlying diseases via the nose up to the height of the uvula, and 1 ml of control (water) and different concentrations of capsinoid solutions (0.1, 0.01, 0.001 µM) were administered in drop to measure a latent time between administration of the solution and occurrence of swallowing reflex (sec, a time between elevation of the hyoid bone and down of the hyoid bone). The results are shown in Table 1. In addition, the mean latent time of the three subjects is shown in FIG. 1, where the value of the control is defined as 100%. In the case of the capsinoid administration group, as compared with the control, the swallowing reflex was significantly improved, and concentration-dependent shortening of the time of the swallowing reflex was observed as shown in FIG. 1.

TABLE 1

| Patient (sex, age) | Underlying disease | Control (water) | 0.1 µM | 0.01 µM | 0.001 µM |
|---|---|---|---|---|---|
| A (male, 85 years old) | Patient after gastrostomy | 10.25 | 4.05 | 8 | 7.13 |
| B (female, 82 years old) | Patient after surgery for esophagus cancer | >60 | 23.3 | 31 | — |
| C (male, 69 years old) | Patient suffering from recurrent aspiration pneumonia, after cerebral infarction | 43 | 27 | 27 | — |

INDUSTRIAL APPLICABILITY

The agent for ameliorating dysphagia of the present invention can ameliorate dysphagia and improve QOL (quality of life) of a patient suffering from dysphagia.

The invention claimed is:
1. A method of ameliorating dysphagia comprising administering a composition containing an effective amount of a capsinoid to a subject suffering from dysphagia, wherein said composition contains capsaicinoid in an amount such that amelioration of dysphagia by administering said composition is provided without causing pungency, and wherein said administering is orally and said composition is a gum or a troche.

2. The method of claim 1, wherein the capsinoid content is 1 nmol/kg to 10 mmol/kg.

3. The method of claim 1, wherein the composition is a troche.

4. The method of claim 1, wherein the composition is a gum.

5. The method of claim 1, wherein said administering comprises administering the capsinoid in an amount ranging from 0.001 nmol to 1 mmol/dose.

6. The method of claim 1, wherein said administering comprises administering the capsinoid in an amount ranging from 0.01 nmol to 0.01 mmol/dose.

7. The method of claim 1, wherein said administering comprises administering the capsinoid in an amount ranging from 0.01 nmol to 10 nmol/dose.

8. The method of claim 1, wherein said capsinoid is at least one selected from the group consisting of capsiate, dihydrocapsiate, and nordihydrocapsiate.

9. The method of claim 1, wherein capsinoid is a fatty acid ester of various linear or branched fatty acids and vanillyl alcohols, whose fatty acid chain comprises 8 to 10 carbon atoms.

10. The method of claim 9, wherein the vanillyl alcohol is vanillyl decanoate, vanillyl nonanoate, or vanillyl octanoate.

11. The method of claim 1, wherein capsinoid is at least capsiate (4-hydroxy-3-methoxybenzyl(E)-8-methyl-6-nonenoate).

12. The method of claim 1, wherein capsinoid is at least dihydrocapsiate (4-hydroxy-3-methoxybenzyl 8-methyl-nonanoate).

13. The method of claim 1, wherein capsinoid is at least nordihydrocapsiate (4-hydroxy-3-methoxybenzyl 7-methyl-octanoate).

14. The method of claim 1, wherein said capsinoid is brought into contact with the oral cavity and/or pharynx.

15. A method of ameliorating dysphagia comprising administering a composition containing an effective amount of a capsinoid to a subject suffering from dysphagia, wherein said composition contains capsaicinoid in an amount such that amelioration of dysphagia by administering said composition is provided without causing pungency, and wherein said effective amount of said capsinoid is brought into contact with the oral cavity and/or pharynx.

16. The method of claim 15, wherein said composition is a food.

17. The method of claim 16, wherein the capsinoid content is 1 nmol/kg to 10 mmol/kg.

18. The method of claim 16, wherein the food composition is a troche.

19. The method of claim 15, wherein said administering is orally.

20. The method of claim 15, wherein said administering comprises administering the capsinoid in an amount ranging from 0.001 nmol to 1 nmol/dose.

21. The method of claim 15, wherein said administering comprises administering the capsinoid in an amount ranging from 0.01 nmol to 0.01 nmol/dose.

22. The method of claim 15, wherein said administering comprises administering the capsinoid in an amount ranging from 0.01 nmol to 10 nmol/dose.

23. The method of claim 15, wherein said capsinoid is at least one selected from the group consisting of capsiate, dihydrocapsiate, and nordihydrocapsiate.

24. The method of claim 15, wherein capsinoid is a fatty acid ester of various linear or branched fatty acids and vanillyl alcohols, whose fatty acid chain length comprises 8 to 10 carbon atoms.

25. The method of claim 24, wherein the vanillyl alcohol is vanillyl decanoate, vanillyl nonanoate, or vanillyl octanoate.

26. The method of claim 15, wherein capsinoid is at least capsiate (4-hydroxy-3-methoxybenzyl(E)-8-methyl-6-nonenoate).

27. The method of claim 15, wherein capsinoid is at least dihydrocapsiate (4-hydroxy-3-methoxybenzyl 8-methyl-nonanoate).

28. The method of claim 15, wherein capsinoid is at least nordihydrocapsiate (4-hydroxy-3-methoxybenzyl 7-methyl-octanoate).

29. The method of claim 1, wherein the ratio of capsinoid and capsaicinoid in said composition is from 2,000:1 to 1:0.

30. The method of claim 1, wherein the ratio of capsinoid and capsaicinoid in said composition is from 1,900:1 to 1:0.

31. The method of claim 15, wherein the ratio capsinoid and capsaicinoid in said composition is from 2,000:1 to 1:0.

32. The method of claim 15, wherein the ratio capsinoid and capsaicinoid in said composition is from 1,900:1 to 1:0.

* * * * *